United States Patent
Wikander

(10) Patent No.: US 6,985,554 B2
(45) Date of Patent: Jan. 10, 2006

(54) MAMMOGRAPHY COMPRESSION PLATE AND X-RAY DIAGNOSTIC APPARATUS EMPLOYING SAME

(75) Inventor: Susanne Wikander, Haninge (SE)

(73) Assignee: Siemens Aktiengesellschaft, Munich (DE)

(*) Notice: Subject to any disclaimer, the term of this patent is extended or adjusted under 35 U.S.C. 154(b) by 62 days.

(21) Appl. No.: 10/691,407

(22) Filed: Oct. 22, 2003

(65) Prior Publication Data

US 2004/0125912 A1 Jul. 1, 2004

(30) Foreign Application Priority Data

Oct. 22, 2002 (SE) .............................. 0203107

(51) Int. Cl.
*A61B 6/04* (2006.01)

(52) U.S. Cl. ........................................ 378/37
(58) Field of Classification Search .................... 378/37
See application file for complete search history.

(56) References Cited

U.S. PATENT DOCUMENTS

| | | | |
|---|---|---|---|
| 3,971,950 A | 7/1976 | Evans et al. | |
| 4,090,084 A | 5/1978 | Epstein et al. | |
| 4,943,986 A | 7/1990 | Barbarisi | |
| 5,029,193 A | * 7/1991 | Saffer | 378/37 |
| 5,479,927 A | 1/1996 | Shmulewitz | |
| 5,999,836 A | 12/1999 | Nelson et al. | |

FOREIGN PATENT DOCUMENTS

| | | |
|---|---|---|
| WO | WO 99/56623 | 11/1999 |
| WO | WO 01/66013 | 9/2001 |

* cited by examiner

*Primary Examiner*—Craig E. Church
(74) *Attorney, Agent, or Firm*—Schiff Hardin LLP

(57) ABSTRACT

A compression plate for a mammography device has four sides and a base, and a bracket attached at one of the sides for moveably mounting the compression plate to an arm, to which an x-ray source also is mounted.

To allow both large and small breasts to be imaged in various exposures, including horizontal exposures, with the breast centered on the subject table between the table and the plate, and to allow tissues outside of the compressed breast also to be imaged, the sides of the plate that terminate on the side attached to the bracket are fashioned such that at least a part of their widths is slanted inwardly in the direction of the base of the plate, preferably along the entire lengths of the sides.

8 Claims, 2 Drawing Sheets

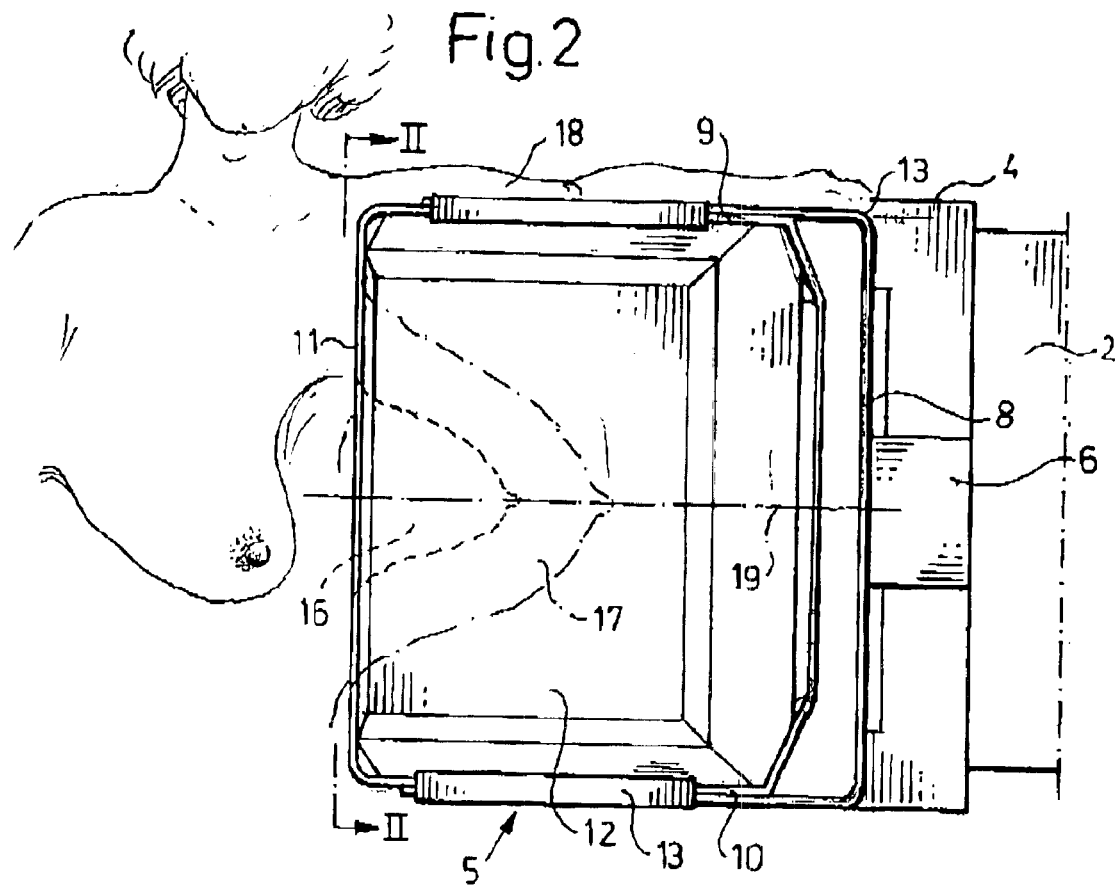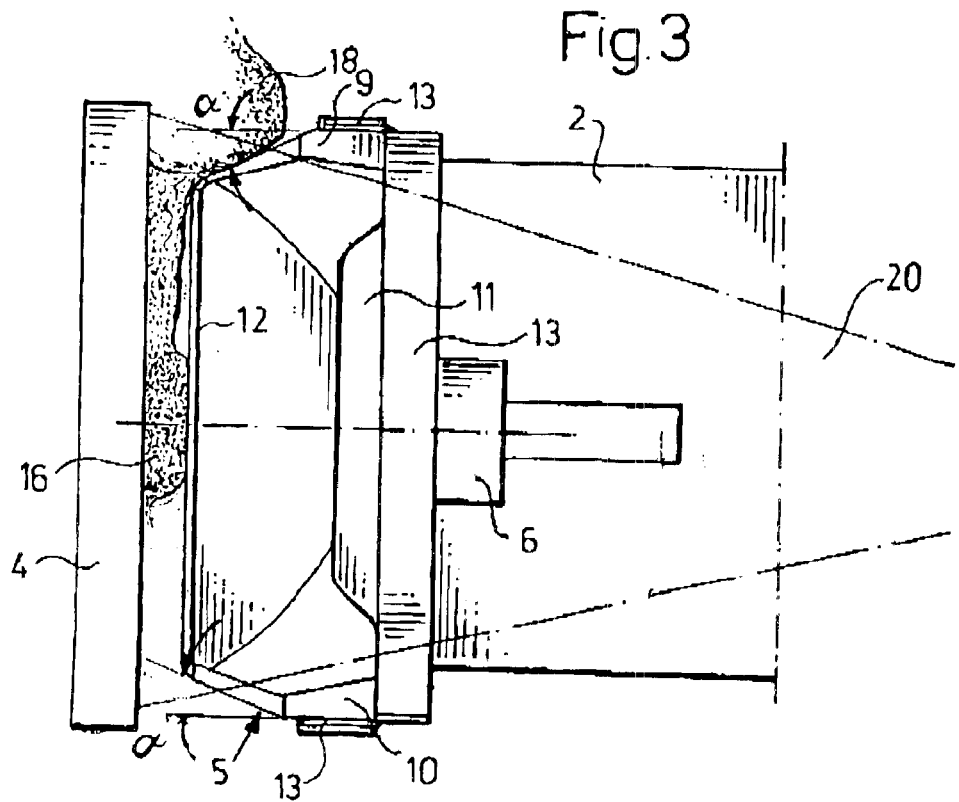

MAMMOGRAPHY COMPRESSION PLATE AND X-RAY DIAGNOSTIC APPARATUS EMPLOYING SAME

BACKGROUND OF THE INVENTION

1. Field of the Invention

The invention concerns a compression plate for a mammography device of the type wherein the plate has four sides and a base, with a bracket attached to the a first of the sides. The invention additionally concerns an x-ray diagnostic device with such a compression plate.

2. Description of the Prior Art

A mammography device basically includes a stand with an arm that carries an x-ray tube and a subject table as well as a compression plate of the above type arranged between the x-ray tube and the subject table. The plate is connected by the bracket to the arm and can be moved along the arm. In such devices, the arm is rotatably connected to the stand by a connector. A mammography device of this type is described in the specification sheet of the company Bennet Trex Medical with the title "The MF-150 Mammography System". Furthermore, a larger number of compression plates are shown therein for selection, which can be mounted on the mammography device. These compression plates are, like most plates, provided with a metal frame. The metal frame that is attached to the bracket runs along the side to which the bracket is attached and along at least one part of another side that joins the aforementioned side. The metal frame is provided to stabilize the compression plate. The two sides are arranged lateral to the base of the compression plate.

Smaller compression plates are used in the examination of relatively small breasts, and when the breasts are of normal size or are larger than normal, the x-ray technician changes to one of the larger compression plates. This ensues primarily so that the x-ray technician can center, on the subject table, the breast to be compressed, such that the center ray of the x-ray beam intersects the hypothetical central axis of the breast. In the x-ray exposure obtained such an examination, the divergent x-ray field is less, which results in a clearer and sharper image of the subject.

A further advantage is that, with a compression plate adapted to a breast size, the x-ray technician can easily reach the breast in order to correct, among other things, possible skin folds on the breast before the compression thereof. A disadvantage with breast-adapted compression plates exists in particular in a horizontal exposure, when the technician wants to image organs and tissues above the compressed breast. With a breast-adapted compression plate, it often occurs in such an exposure that the x-ray field also includes the metal frame of the plate, which results an unacceptable x-ray image. A further disadvantage is that an exchange of compression plates dependent on the breast size is time-consuming for the x-ray technician. Additionally, it is relatively expensive to acquire a larger number of compression plates for each mammography device.

SUMMARY OF THE INVENTION

An object of the invention is to provide a compression plate of the type initially described that has a form or shape that allows both large and small breasts to be centered in a horizontal exposure on the subject table between the table and the plate. With such a compression plate, organs and tissues outside of the compressed breast can also additionally be imaged.

This object is inventively achieved in a compression plate and x-ray diagnostic (mammography) apparatus wherein the sides of the plate that terminate at the side to which the bracket is attached are fashioned such that at least one part of their widths is slanted inwardly in the direction of the base of the plate, preferably along the entire length of the side.

The lower part of the widths of the sides preferably is slanted. An x-ray technician can easily center the breast on the subject table in a horizontal exposure of a medium-sized or a large breast. Because the sides of the compression plate are slanted, the breast can be reached easily and therefore can be quickly placed in a desired position. The slanting of the plate contributes and facilitates ability of the x-ray technician shift the compression plate upwardly such that its upper edge comes to lie exactly beneath the collarbone clavicle of the patient, so that tissues above the breast also can be imaged. A further reason why an exposure of tissue above the breast can ensue is that the separation between the sides running parallel to one another (that are stabilized by means of the metal frame) is longer than the separation between the corresponding sides of the base of the compression plate running parallel to one another. The x-ray radiation field thus can be wider than the width of the base of the compression plate, without the metal frames being encompassed within the x-ray field.

In connection with a horizontal exposure, in particular of a relatively small breast, the patient can use the slanting of the compression plate (that, given a compression, forms a depression or recess between the subject table and the compression plate) for the purpose of placing an arm inside, which allows the compression plate to be moved relatively high in the armpit. Via this movement of the compression plate with the subject table, a small breast can assume a position allowing it to be easily centered on the subject table. Due to the slanting of the sides of the compression plate, moreover, good access a small breast is achieved during the examination.

In an embodiment of the invention, the angle of the slanting can be between 20° and 40°, preferably 24°.

DESCRIPTION OF THE DRAWING

FIG. 2 is a plan view of a compression plate according to FIG. 1 in connection with a horizontal exposure.

FIG. 3 is a front view of a compression plate according to FIGS. 1 and 2 in connection with a horizontal exposure.

DESCRIPTION OF THE PREFERRED EMBODIMENTS

Figure 1:
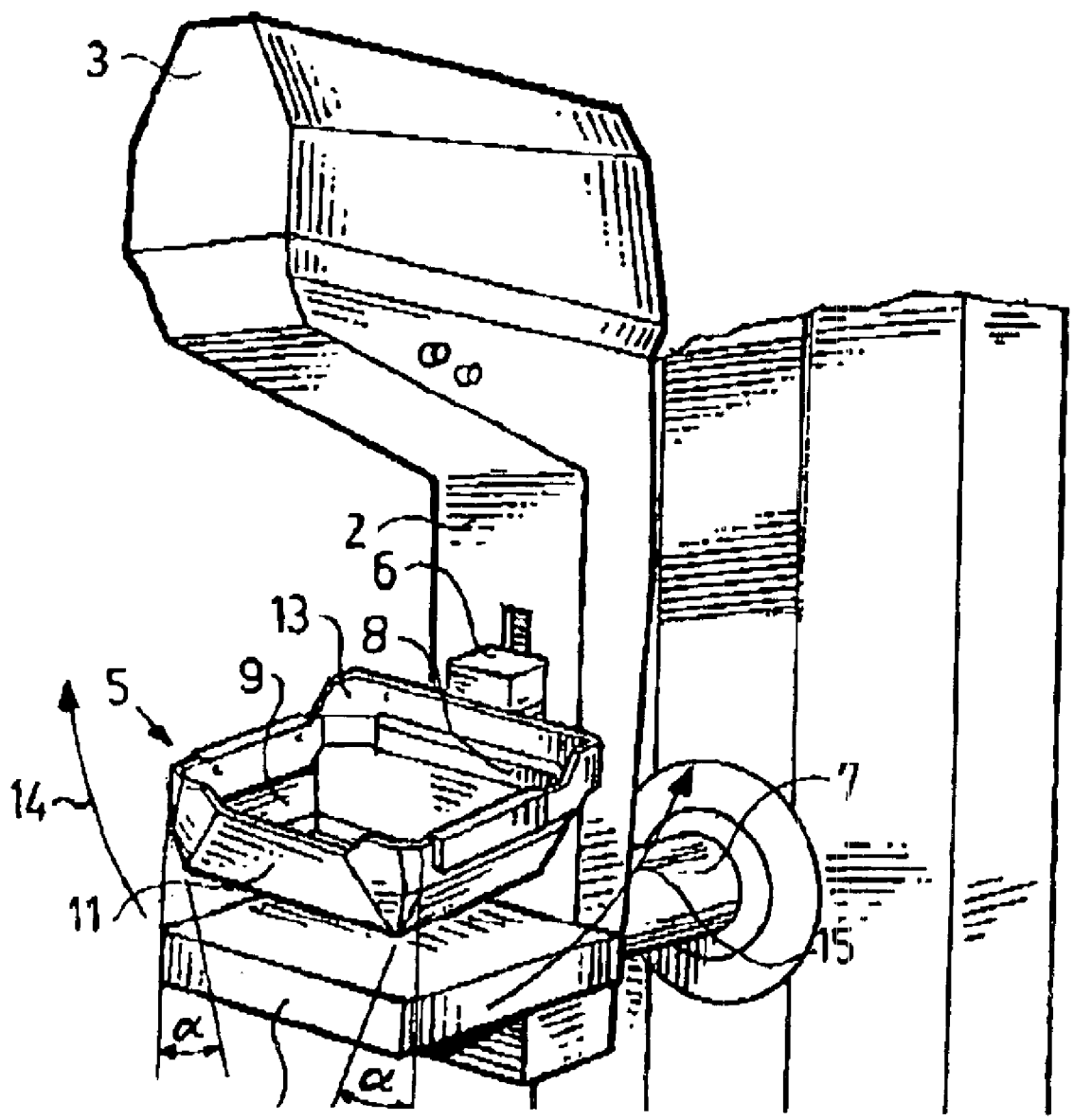
FIG. 1 is a perspective view of a mammography device with a compression plate according to the invention.

In FIG. 1, a mammography device is shown with a stand 1 that carries an arm 2 for an x-ray tube 3 and a subject table 4. A compression plate 5 is arranged between the x-ray tube 3 and the subject table 4 that is connected to the arm 2 via a mounting, that is a bracket 6 in the exemplary embodiment. The compression plate 5 can be moved along the arm 2. The arm 2 is mounted via a shaft 7 to the stand 1 and can be moved along the stand 1 to adjust the height of the arm 2.

The compression plate 5 has four sides 8 through 11 and a base 12. The bracket 6 is arranged in the region of the first side 8, in the exemplary embodiment at the first side 8 of the pate 5, and is connected with the plate 5 by a metal frame 13. The metal frame 13 runs along the side 8 and along larger parts of the sides 9 and 10. It is also shown in FIG. 1 that the lower part of the widths of the sides 9 and 10 are slanted inwardly with a slant angle α in the direction of the base 12 of the plate 5 along the entire lengths of the sides 9, 10. The slant angle α is between 20° and 40°, preferably 24°.

In FIG. 1, the compression plate 5 is shown in a standby position.

When a horizontal exposure of a breast of a patient is to be implemented, the arm 2 (and with it the x-ray tube 3, the subject table 4 and the compression plate 5) is rotated 90° around the shaft 7, either in the direction of the arrow 14 or in the direction of the arrow 15.

In the exemplary embodiment shown in FIG. 2, the x-ray technician has rotated the arm 2 in the direction of the arrow 14, such that the left breast of a patient can be examined. If the patient has a normal-sized or a relatively large breast that should be examined, the x-ray technician can arrange the breast such that the breast is centered on the subject table 4 given a compression, so an optimally sharp x-ray image is acquired. Because the compression plate 5 is slanted in the specified manner, it is relatively simple to access the breast and, if required, to effect a position correction. The outline of a large breast 17 is shown in FIG. 2 with a dashed-dot line.

In FIG. 2, a patient is also shown with a relatively small breast 16. In a horizontal exposure, the above-described problem of placing a small breast in a specified central position in solved because in connection with a compression, a depression exists, running along the sides 9 and 10 (in this exemplary embodiment along the side 9) between the subject table 4 and the compression plate 5. The depression is formed by the slant α. The patient can arrange her arm 18 in this depression such that the compression plate 5 can be moved below the collarbone of the patient. The compression plate 5 and the subject table 4 therefore are moved in relation to the patient and the breast to be imaged in terms of height so that the breast 16 can be placed in a desired position along the center line 19 of the subject table 4 and the compression plate 5.

In FIG. 3, a front view of the compression plate 5 and simultaneously a section along the section line II—II in FIG. 2, are shown. The section here runs partially through the patient, in order to clearly show that the arm 18 of the patient can be placed in the aforementioned depression. In addition, FIG. 3 shows that, given an exposure, the x-ray beam 20 generated by the x-ray tube 3, due to the shape of the compression plate 5 can irradiate, as required, tissues that lie outside of that part of the patient that is compressed by the plate 5, without the x-ray beam 20 encountering the metal frame 13.

In a horizontal exposure of the second breast of the patient, the arm 2 is rotated in the direction of the arrow 15. A compression of this second breast is implement in the same manner as specified in connection with the compression of the first breast.

Due to its advantageous form specified in detail, the compression plate according to the invention can be used with nearly all breast sizes, and therefore seldom or never needs to be exchanged with a larger or smaller compression plate.

Although modifications and changes may be suggested by those skilled in the art, it is the intention of the inventor to embody within the patent warranted hereon, all changes and modifications as reasonably and properly come within the scope of her contribution to the art.

What is claimed is:

1. A mammography compression plate comprising:
   four lateral sides connected to a base, each of said four lateral sides having a width and a length, with a first of said lateral sides being adapted for connection to a mounting bracket; and
   said four lateral sides including two lateral sides that respectively terminate at said first of said lateral sides, each of said two lateral sides having at least a portion of said width slanted inwardly toward said base.

2. A compression plate as claimed in claim 1 wherein said portion comprises a lower portion of the width of each of said two sides.

3. A compression plate as claimed in claim 1 wherein said portion is slanted at an angle in a range between 20° and 40°.

4. A compression plate as claimed in claim 3 wherein said portion is slanted at an angle of 24°.

5. An x-ray diagnostic device for mammography examinations comprising:
   a supporting stand;
   an arm moveably mounted to said supporting stand;
   an x-ray tube and a subject table attached to said arm spaced from each other;
   a compression plate disposed between said x-ray tube and said subject table;
   a bracket connecting said compression plate to said arm and allowing movement of said compression plate relative to said subject table to allow compression of a female breast between the compression plate and the subject table; and
   said compression plate comprising four lateral sides and a base, with a first of said lateral sides being connected to said bracket and two of said lateral sides respectively terminating at said first of said lateral sides, said two lateral sides each having a width with portion thereof slanted inwardly toward said base.

6. A compression plate as claimed in claim 5 wherein said portion comprises a lower portion of the width of each of said two sides.

7. A compression plate as claimed in claim 5 wherein said portion is slanted at an angle in a range between 20° and 40°.

8. A compression plate as claimed in claim 7 wherein said portion is slanted at an angle of 24°.

* * * * *